United States Patent [19]

Nanguneri

[11] Patent Number: 5,705,714
[45] Date of Patent: Jan. 6, 1998

[54] REMOVAL OF METALS AND COLOR BODIES FROM CHEMICALLY RECYCLED BISPHENOL-A

[75] Inventor: Srikanth Nanguneri, Franciscusberg, Netherlands

[73] Assignee: General Electric Company, Pittsfield, Mass.

[21] Appl. No.: 673,900

[22] Filed: Jul. 1, 1996

[51] Int. Cl.[6] .................................................. C07C 37/68
[52] U.S. Cl. .............................................................. 568/724
[58] Field of Search ............................................... 568/724

[56] References Cited

U.S. PATENT DOCUMENTS

| | | | |
|---|---|---|---|
| 4,885,407 | 12/1989 | Fox | 568/724 |
| 5,382,708 | 1/1995 | Kissinger | 568/702 |

*Primary Examiner*—José G. Dees
*Assistant Examiner*—Barbara Badio

[57] ABSTRACT

An improved process for the purification of solid dihydric phenol, preferably bisphenol-A recovered from a polymer containing the reaction residue of dihydric phenol units in the polymer structure by essentially dry distilling dihydric phenol in the presence of about 0.005 to about 0.05 weight percent of hypophosphorous acid based on the weight of dihydric phenol.

8 Claims, No Drawings

1

REMOVAL OF METALS AND COLOR BODIES FROM CHEMICALLY RECYCLED BISPHENOL-A

FIELD OF THE INVENTION

This instant invention relates to a process of removing metals and color bodies from dihydric phenol units in their polymer structure. The process employed is the dry distillation of crude dihydric phenol in the presence of hypophosphorous acid. More specifically, the dihydric phenol is bisphenol-A. The purified dihydric phenol is then suitable as a reactant for producing such materials as polycarbonates, epoxies, and the like, wherein dihydric phenol is a constituent in the chemical reaction.

BACKGROUND OF THE INVENTION

With the advent of manufactured materials, particularly thermoplastic materials, the problem of dealing with abandoned thermoplastic products and materials has been an increasing problem. Many thermoplastic materials are not substantially biodegradable. Steps have been taken and are continuing to be taken and developed to recycle thermoplastic products. Unfortunately, recycling involves thermal processing of the thermoplastic and as such generally results in degradation of the thermoplastic both with respect to its chemical and physical properties thereby affecting its performance compared to virgin material. Each time a plastic is exposed to thermal processing, the properties thereof can become degraded such as impact resistance, deformation under load and temperature, tensile strength, flexural strength, elongation, flow behavior, etc. As more and more thermoplastic products are employed in preparing consumer products, the plastic scrap dilemma becomes ever increasing. Clearly, a method of recovering scrap plastics and converting them into useful chemical constituents would be an asset to the public and the plastics industry.

U.S. Pat. No. 4,885,407 describes a process of recovering a dihydric phenol particularly bisphenol-A from scrap or otherwise abandoned aromatic polyesters such as polycarbonates. The process involves contacting the polycarbonate, for example, with an aqueous ammoniacal solution and a solvent for the polycarbonate such as methylene chloride to form two liquid phases, with the top phase being aqueous and the bottom phase being methylene chloride phase. The methylene chloride dihydric phenol solution can simply be heated to its boiling point wherein the methylene chloride and the ammonia are removed, leaving the dihydric phenol. Alternatively, the methylene chloride may be added to a hot solvent which boils at a higher temperature than the methylene chloride and in which the dihydric phenol (bisphenol-A) is insoluble at a lower temperature. Then as the solvent cools, the substantially purified bisphenol-A crystallizes therefrom. There is no suggestion or disclosure of dry distilling dihydric phenol in the presence of hypophosphorous acid ($H_3PO_2$) to obtain a highly purified dihydric phenol, particularly bisphenol-A.

U.S. Pat. No. 5,382,708 on the other hand discloses a process for purifying bisphenol-A by adding hypophosphorous acid to a bisphenol-A composition as produced and then subjecting the composition to distillation. The process is directed to purification of virgin bisphenol prepared by the acid catalyzed condensation of a phenol with an aldehyde or a ketone such as acetone. After the reaction, the bisphenol-A in the product stream can be recovered using a distillation train wherein the component bisphenol-A is separated by distillation with hypophosphorous acid. The distillation with hypophosphorous acid removes color impurities, tars and reduces significant logs in bisphenol-A yields.

However, with scrap or internal waste virgin polymer compositions containing the reaction residue of dihydric phenol units in their structure, a different criteria is necessary, i.e., the need to remove undesirable color impurities, metals and metal-complexing species that cause color in BPA during recycling of such scrap or internal waste polymer compositions, which are either already present in the polymer from the formulation thereof with pigments or from the metal handling equipment itself.

SUMMARY OF THE INVENTION

It has been surprisingly discovered that crude dihydric phenol obtained by chemical means from polymers containing the reaction residue of dihydric phenol units in its structure can be purified by a very simple and surprisingly effective process of dry distillation in the presence of hypophosphorous acid. The quality of bisphenol-A obtained by this process is of extremely high purity. As crude BPA is obtained by chemical means, the crude BPA contains color bodies and metal complexes which can also cause undesirable color bodies. These color bodies can come from the molding and/or extrusion formulations and/or from metals of the equipment employed either during processing or recovering of plastics for recycling, such as grinding, handling equipment and the like.

The surprising discovery is that the crude BPA obtained from scrap or abandoned polymer can be purified by dry distilling the BPA in the presence of hypophosphorous acid. More specifically, crude BPA obtained from the process of U.S. Pat. No. 4,885,407 and U.S. patent application Ser. No. 08/673,990 filed of even date herewith can be purified by the process of the instant invention, both of which are hereby incorporated herein by reference.

DETAILED DESCRIPTION OF THE INVENTION

The instant invention is directed to an improved process of purifying recovered dihydric phenol, particularly bisphenol-A (hereinafter BPA), by dry distillation of crude BPA in the presence of hypophosphorous acid. More specifically, hypophosphorous acid is added to the BPA solution in an amount of about 0.005 to about 0.05 weight percent based on the weight of BPA. It is believed that the hypophosphorous acid inhibits metal complexing with BPA species during thermal processing which is the source of undesirable color bodies. While the BPA employed in preparing polymers such as polycarbonates or polyarylates is of high purity usually at least about 95 weight % and preferably at least about 99 weight % pure, the crude BPA recovered from the polymeric form contains undesirable color bodies and/or metals which can complex with BPA species to form additional undesirable color bodies. Such impurities are removed by the essentially dry distillation of the crude BPA in the presence of hypophosphorous acid. The purity obtained by the improved process of this invention is at least about 95 weight % pure and preferably at least about 99 weight % pure and specifically greater that 99 weight % pure.

Preferably, this process is applicable to BPA recovered by the ammoniacal process of Ser. No. 08/673,990 filed of even date herewith and which is incorporated herein by reference. That process briefly comprises granulating a thermoplastic composition containing a thermoplastic polymer having in its structure the reaction residue of dihydric phenol units, treating the granulated particles with an organic swelling agent, such as methanol, for a time sufficient to swell the particles, contacting the particles with an aqueous ammoniacal solution, such as ammonium hydroxide, thereby forming a solid and a liquid phase, distilling ammonia and methanol from the liquid phase, the residue of which contains dissolved urea and partially precipitated dihydric phenol, adding sufficient water to the residue of the distillation of the liquid phase, thereby forming a liquid and solid phase since dihydric phenol is insoluble in water, and then recovering the precipitated dihydric phenol such a bisphenol-A. The bisphenol-A recovered is crude bisphenol-A containing color bodies and metals. The metals upon exposure to thermal processing could form metal complexes thereby affecting the color of BPA. The color bodies and metal impurities are dry distilled in the presence of hypophosphorous acid which inhibits the BPA species from forming metal complexes upon exposure to thermal processing.

The instant invention is applicable to the purification of any dihydric phenol in solid form since the distillation process of the invention is dry distillation and may be at a pressure that may be above atmospheric, atmospheric or below atmospheric pressure (namely, under a vacuum). Dry distillation under a vacuum is the preferred distillation condition.

The dihydric phenol (bisphenol-A) obtained in accordance with the teaching of U.S. Pat. No. 4,885,407 in the solid form may still have color bodies and/or metals that can form undesirable impurities. If a high purity grade BPA is wanted, then the dry BPA of 4,885,407 may also be subject to the process of this invention to remove impurities.

While this invention is disclosed in terms of dihydric phenol, the most well known dihydric phenol is bisphenol-A employed in preparing polycarbonates. A high purity grade bisphenol-A is most desired for producing aromatic polycarbonates. Aromatic polycarbonates are also well known in the polymer field and their preparation is fully disclosed in the patent literature. Briefly, the process comprises reacting a bisphenol-A with a carbonate precursor, such as phosgene, a haloformate or a carbonate ester. This may be prepared in accordance with methods set forth in U.S. Pat. Nos. 4,018,750, 4,123,326 or 3,153,008, as well as other patent references.

As stated previously, the polymers containing the reaction residue of dihydric phenol units in their structure may be aromatic polyesters, such as polycarbonates, copolyestercarbonates, polyarylates or mixtures thereof, or mixtures thereof with other polymers and/or materials. Such other polymers include polyamide (nylon), polybutylene-terephthalate (PBT), polyethylene-terephthalate (PET), polyphenylene ether, acrylonitrile-butadiene-styrene (ABS), and the like. Other materials may include fillers and/or reinforcing agents, such as glass fibers, carbon, other minerals, pigments, rubber (natural or synthetic), impact modifiers and the like. These materials, and other polymers, are separable from the polymer containing the dihydric phenol residue units.

The following examples are intended to illustrate this invention and are not intended to limit or narrow the inventive concepts disclosed herein.

EXAMPLE 1

Scrap polycarbonate sheet (about 99.5 weight % polycarbonate) was granulated and dihydric phenol (bisphenol-A) was recovered in accordance with the ammoniacal process described below.

To about 10.5 grams of the granulated polycarbonate sheet in a laboratory beaker, 45 ml of methanol (100%) was added. The mixture was stirred at room temperature for about 60 minutes. The polycarbonate particles were observed to swell effectively in methanol. About 45 ml of a 25% by weight aqueous ammonium hydroxide solution (a 50:50 weight ratio of ammonium hydroxide to methanol) was added to the swollen particle-methanol mixture and agitated for about 1 hour at a temperature of about 40° C. Two phases were formed consisting of a solid phase and a liquid phase. The phases were separated by filtration and the solid phase was dried and weighed. It was determined that the solid phase was about 1 weight % (0.1 g) of the weight of the total polycarbonate sample.

The liquid phase was then distilled to remove ammonia and methanol during which the ammonium salt of the dihydric phenolate was converted to the dihydric phenol form or bisphenol-A. The residue was a solid consisting of urea and bisphenol-A since upon distillation, the ammonium salt of bisphenol-A was transferred or converted to bisphenol-A. Sufficient water was added to the essentially aqueous solution of dissolved urea and partially precipitated bisphenol-A to completely separate the bisphenol-A from the urea liquid phase. Since urea is soluble in water, two phases were formed, a solid phase which was bisphenol-A since it is insoluble in water and a liquid phase which was an aqueous solution of urea. The bisphenol-A that was recovered by filtration was dried and weighed.

For comparison purposes, other samples of bisphenol-A were also analyzed for color. These samples were polycarbonate sheet scrap BPA used in this Example 1 (Sample 1), crude BPA sample from commercial plant production thereof that is fed into a crystallizer (Sample 2), polycarbonate scrap BPA treated with activated charcoal (Sample 3), BPA recovered in accordance with this Example and dry distilled but without hypophosphorous acid (Sample 4) and BPA recovered in accordance with this Example and distilled with hypophosphorous acid (Sample 5). The amount of hypophosphorous acid employed in Sample 5 was about 0.002 weight % based on the weight of the sample. The hypophosphorous acid employed was a 50 weight % aqueous solution of the hypophosphorous acid.

Distillation was carried out under a vacuum of about 1.0 mm Hg. The results were as follows:

TABLE 1

| | Sample | | | | |
|---|---|---|---|---|---|
| | 1 | 2 | 3 | 4 | 5 |
| UV* (350 nm) initial absorbance | 25.0 | 2.50 | 1.60 | 2.16 | 0.15 |

*UV - ultra violet light

The quality of the BPA was determined by ultra violet light (UV) initial absorbance of the sample of BPA at 350 nm (nanometers). Impurities in BPA cause a higher absorbance than pure BPA. A spectrophotometer (UV/VISUAL) was employed using a 1.0 gram sample dissolved in 10 ml of methanol solvent and measured at 350 nm. A 5 cm quartz cuvette was employed to hold the sample. The spectrophotometer was switched to 350 nm. The cuvette was rinsed, filled with methanol and placed in the spectrophotometer. The absorbance scale was adjusted to 0.0 nm. The cuvette was then rinsed and filled with 10 ml of the BPA-methanol solution. The initial absorbance was then read with the results reported in Table 1.

As seen from the results, the essentially dry distillation of the BPA recovered in accordance with Example 1 in the presence of hypophosphorous acide was of a higher purity compared to the other samples.

While the invention has been described and illustrated in connection with certain preferred embodiments thereof, it will be apparent to those skilled in the art that the invention is not limited thereto. Accordingly, it is intended that the appended claims cover all modifications which are within the spirit and scope of this invention.

What is claimed is:

1. A process for recovering bisphenol-A from a thermoplastic polymer composition having a residue of bisphenol-A units in its polymer structure comprising granulating the polymer composition, treating the granulated particles with an organic swelling solvent that is miscible with water for a time sufficient to swell the granulated particles, contacting the swelled particles with an aqueous ammoniac solution at a temperature of at least about 25° C. forming a liquid and a solid phase, recovering the liquid phase, distilling ammonia and the organic swelling solvent from the recovered liquid phase, adding water to the residue of the distillation step forming a liquid and a solid phase, which solid phase is crude bisphenol-A, recovering the crude bisphenol-A and essentially dry distilling the crude bisphenol-A in the presence of about 0.005 to about 0.05 weight percent of hypophosphorous acid based on the weight of bisphenol-A whereby undesirable color impurities, metals and metal-complexing species are removed and the bisphenol-A is at least 95 weight % pure bisphenol-A.

2. The process of claim 1 wherein hypophosphorous acid is an aqueous solution of the hypophosphorous acid.

3. The bisphenol-A of claim 1 wherein the purity is at least 99 weight % pure bisphenol-A.

4. The process of claim 1 wherein the organic swelling agent is methanol.

5. The process of claim 1 wherein the hypophosphorous acid is a aqueous solution thereof.

6. The process of claim 5 wherein the purity of bisphenol-A obtained is at least 99 weight percent of bisphenol-A.

7. The process of claim 6 wherein the distillation is under vacuum.

8. The process of claim 1 wherein the distillation is under vacuum.

* * * * *